United States Patent [19]

VanRheenen

[11] Patent Number: 4,614,621

[45] Date of Patent: Sep. 30, 1986

[54] ETHYNYLATION OF 16-METHYLENE-17-KETO STEROIDS

[75] Inventor: Verlan H. VanRheenen, Portage, Mich.

[73] Assignee: The Upjohn Company, Kalamazoo, Mich.

[21] Appl. No.: 602,300

[22] Filed: Apr. 20, 1984

[51] Int. Cl.$^4$ ............................................. C07J 5/00
[52] U.S. Cl. ............................... 260/397.45; 540/87; 540/88
[58] Field of Search ............ 260/397.45, 239.55, 260/397.4, 239.55 R

[56] References Cited

U.S. PATENT DOCUMENTS

| | | | |
|---|---|---|---|
| 2,272,131 | 2/1942 | Ruzecka et al. | 260/397.4 |
| 2,723,280 | 11/1955 | Inhoffen et al. | 260/397.5 |
| 2,843,609 | 7/1958 | Colton | 260/397.5 |
| 2,877,240 | 3/1959 | Campbell et al. | 260/397.4 |
| 3,275,666 | 9/1966 | Siegmann | 260/397.5 |
| 3,470,217 | 9/1969 | Ginsig | 260/397.4 |
| 3,704,253 | 11/1972 | Stein et al. | 260/397.4 |
| 4,041,055 | 8/1977 | Shephard et al. | 260/397.3 |
| 4,055,562 | 10/1977 | Christiansen | 260/239.55 R |
| 4,320,236 | 3/1982 | Wiederkehr | 568/813 |
| 4,526,720 | 7/1985 | Van Rheenen et al. | 260/397.4 |

OTHER PUBLICATIONS

Steroids, Fieser & Fieser, Reinhold Publishing 1959, pp. 557–591.
J. Am. Chem. Soc. 78, 2477 (1956).
J. Org. Chem. 34, 435 (1969).
J. Chem. Soc., 4765 (1956).
J. Mol. Structure 42, 251 (1977), J. B. Moffat.
J. Am. Chem. Soc. 98, 4778 (1976), A. Streitwieser.
J. Org. Chem. 40, 2250 (1975).
Chem. Ind. (Milan) 42, 251 (1960).
Chem. Abstr. 54, 19250 (1960).
J. Org. Chem. 43, 4679 (1978).
J. Med. Chem. 11, 924 (1968).
Reagents for Organic Synthesis, vol. 1, Wiley, New York, 1967, p. 573.

Primary Examiner—Elbert L. Roberts
Attorney, Agent, or Firm—Bruce Stein

[57] ABSTRACT

The process of the present invention transforms 16-methylene-17-keto steroids (I) to the corresponding 17α-ethynyl-17β-hydroxy-16-methylene steroids (II).

20 Claims, No Drawings

ETHYNYLATION OF 16-METHYLENE-17-KETO STEROIDS

BACKGROUND OF THE INVENTION

Ethynylation of 17-keto steroids to produce commercially important 17α-ethynyl-17β-hydroxy steroids is well known to those skilled in the art. See, for example, U.S. Pat. Nos. 2,272,131, 2,843,609, 2,723,280, 3,275,666, 2,877,240, 3,470,217, 4,041,055, Steroids by Fieser and Fieser, Reinhold Publishing Co., New York, 1959, 557–591, and J. Am. Chem. Soc. 78, 2477 (1956).

The general method of ethynylation is to react the 17-keto steroid with dipotassium acetylide. The advantage of the dipotassium acetylide process is that it can be used with $\Delta^4$-3-keto steroids without having to protect the 3-keto group. However, that procedure cannot be used with 16α-methyl-17-keto-, 16β-methyl-17-keto- or 16-methylene-17-keto-steroids for well known reasons. Commercially the ethynylation of 16α- or 16β-methyl- as well as 16-methylene-17-keto steroids is important because the 17α-ethynyl-17β-hydroxy-16α-methyl-, 17α-ethynyl-17β-hydroxy-16β-methyl- and 17α-ethynyl-17β-hydroxy-16-methylene-steroids can be transformed to dexamethasone, betamethasone and melengestrol acetate.

Metallo-acetylides other than dipotassium acetylide are known. Monosodium acetylide is known, see U.S. Pat. No. 3,470,217 and R. J. Tedeschi, et al., J. Org. Chem. 34, 435 (1969). Mono- and bis-magnesium acetylides are known, see L. Skattebol, et al., J. Chem. Soc. 4765 (1956). Although the use of magnesio-acetylides has been reported for 17α-ethynyl introduction, substantial dimer formation results with both mono- and bis-magnesioacetylides, see U.S. Pat. No. 3,704,253.

Lithioacetylide reagents exhibit substantially different reactivity in many cases from other metallo-acetylides. This fact and the ready availability of n-butyllithium has resulted in the extensive use of these reagents in syntheses. The covalent nature of the carbon-lithium bond has been the subject of many theoretical and experimental investigations, see, for example, J. B. Moffat, J. Mol. Structure 42, 251 (1977) and A. Streitwieser, et al., J. Am. Chem. Soc. 98, 4778 (1976).

M. M. Midland in J. Org. Chem. 40, 2250 (1975) reported reacting n-butyllithium with acetylene in THF at low temperature ($< -70°$) and in dilute solution to produce monolithium acetylide. Monolithium acetylide is a valuable reagent for the preparation of ethynyl carbinols and terminal acetylenes, see Fieser and Fieser, Reagents for Organic Synthesis, Vol. 1, Wiley, New York, 1967, p 573. Midland found that warming or attempting to generate a more concentrated solution resulted in disproportionation to the insoluble dilithium acetylide and acetylene. This disproportionation is an important disadvantage and occurs in the absence of a complexing agent, see Corbellini et al., Chem. Ind. (Milan) 42, 251 (1960) and Chem Abstr. 54, 19250 (1960). To reduce or prevent the disproportionation the monolithium acetylide is usually prepared in liquid ammonia, which presumably serves as an appropriate complexing agent. An amine such as ethylenediamine can also be used to stabilize monolithium acetylide. Ethylenediamine so greatly stabilizes monolithium acetylide that monolithium acetylide is sold commercially as an ethylenediamine complex. Ethylenediamine while stabilizing monolithium acetylide to the point it can be sold commercially actually reduces the reactivity to the point it is not useful for many ethynylation procedures.

U.S. Pat. No. 4,055,562 used monolithium acetylide to ethynylate 17-keto steroids unsubstituted in the $C_{16}$ position. The monolithium acetylide was prepared by bubbling acetylene into THF held at $-70°$ under anhydrous conditions followed by addition of butyllithium. The 17-keto steroid was added to the unstabilized monolithium acetylide and the mixture stirred for 3 hr at $-70°$ to produce the 17α-ethynyl-17β-hydroxy steroid product.

U.S. Pat. No. 4,320,236 discloses the use of a monolithium acetylideammonia complex (which is well known to those skilled in the art) to ethynylate ketones at below about 30°. The examples in U.S. Pat. No. 4,320,236 disclose ethynylation reaction temperatures of $-50°$ to 10°. The unsaturated acyclic ketones ethynylated in U.S. Pat. No. 4,320,236 are very reactive whereas the steroidal 16-methylene-17-ketones are highly substituted sterically hindered cyclopentanones and therefore much less reactive.

The addition of a lithiated acetylene species to a 16β-methyl-17-keto-steroid in 92% yield was reported by G. Neef, et al., in J. Org. Chem. 43, 4679 (1978) without giving any experimental data but stating, "The ethynylations were performed according to the procedure of Phillips ..." The procedure of Phillips is set forth in J. Med. Chem. 11, 924 (1968). The results reported by Phillips could not be reproduced; the Phillips procedure consistently gave large amounts (greater than 20%) of irreversible enolization. Neef also reported the addition of a lithiated species to a 16α-methyl-17-keto steroid. The yield Neef reported (72%) is more in keeping with the observed irreversible enolization.

U.S. Pat. No. 3,275,666 discloses alkylation of 16-methylene-17-keto steroids with "a metal derivative of a saturated or unsaturated hydrocarbon." The metal could be a alkali metal or an alkaline earth metal compound. In Example II, ethylbromide, magnesium and acetylene were used to produce a 17α-ethynyl-17β-hydroxy-16-methylene steroid. In Example XI, ethylmagnesiumbromide/THF/nitrogen and THF saturated with acetylene were mixed and used to react with a 17-keto-16-methylene steroid to produce a 17α-ethynyl-17β-hydroxy-16-methylene steroid. U.S. Pat. No. 3,275,666 (Examples I and X) used lithium with methyl iodide for alkylation, not ethynylation.

The process of the present invention uses monolithium acetylide and obtains 17α-ethynylation without destruction of the 16-methylene group. The 16-methylene-17-keto steroids (I) react with the monolithium acetylide producing a 17α-ethynyl-17β-hydroxy-16-methylene steroid (II) without the problems expected from reaction with the methylene group α to the 17-keto group.

SUMMARY OF THE INVENTION

Disclosed is a process for the prepartion of a $C_3$ protected 17α-ethynyl-17β-hydroxy-16-methylene steroid (II A,C) which comprises (1) contacting a $C_3$ protected 17-keto-16-methylene steroid (I A,C) with stabilized monolithium acetylide in a dry solvent at a temperature of about 0° or less (2) maintaining the reaction temperature at about 0° or less and (3) quenching with a quenching agent.

Further disclosed is a process for the preparation of a 17α-ethynyl-17β-hydroxy-16-methylene steroid (II B) which comprises (1) contacting a 17-keto-16-methylene steroid (I B) with stabilized monolithium acetylide in a dry solvent at a temperature of about −20° or less (2) maintaining the reaction temperature at about −20° or less; and (3) quenching with a quenching agent.

DETAILED DESCRIPTION OF THE INVENTION

The 16-methylene-17-keto steroid (I) starting materials are well known to those skilled in the art or can be readily prepared from known compounds by methods well known to those skilled in the art. For example, 16-methylene-17-keto steroids (I) where $R_6$ is methyl, α-fluoro and methylene are known, see U.S. Pat. Nos. 3,166,551, 2,838,942 and 3,980,778 respectively. 16-Methylene-17-keto steroids (I) with C-ring substitution are known, for example, 9α-hydroxy (U.S. Pat. No. 3,065,146), $\Delta^{9(11)}$ (U.S. Pat. No. 4,127,596), 11β-hydroxy and 11-keto (U.S. Pat. No. 2,867,630). Further, these steroids are known in the $C_3$ protected forms, for example, the enol ether (U.S. Pat. No. 3,516,991) and the 3-enamine (U.S. Pat. No. 4,216,159).

The 16-methylene-17-keto steroid (I) starting materials are well known to those skilled in the art. See, for example, U.S. Pat. Nos. 3,275,666, 3,300,521 and 3,641,069, Gazz. Chim. Ital. 91, 672 (1961), Hungarian Pat. No. 019,495 and U.S. Pat. No. 4,416,821.

It is preferred that the 16-methylene-17-keto (I) starting materials be prepared by the process of U.S. Pat. No. 4,416,821.

The 16-methylene-17-keto steroids (IA-IC) starting materials may have variable substituents at positions 1, 6, 9, 10 and 11, as is well known to those skilled in the art. For example, U.S. Pat. No. 4,416,821 discloses 16-methylene-17-keto steroids with $\Delta^1$, 6-fluoro, 6-methyl, 11β-hydroxy, 11-keto, 11α-hydroxy, $\Delta^{9(11)}$, 9β,11β-epoxy, and 9α-fluoro substitution as well as combinations thereof. It is preferred in the $\Delta^4$-3-keto series (A) that $R_6$ be a hydrogen atom, methyl or methylene group but in the $\Delta^{1,4}$-3-keto series (B) that $R_6$ be a hydrogen or fluorine atom.

The 17-keto steroids (IA-IC) may or may not have to have the functionality at $C_3$ protected during the ethynylation reaction of this invention depending on the nature of the steroid A ring (A-C), see Chart B. For the $\Delta^4$-3-keto steroid (A) the $C_3$ ketone is protected as the enol ether (Aa), ketal (Ab), enamine (Ac) or enol ester as is well known in the art, see Chart C. The preferred enol ether (Aa) is the methyl or ethyl ether. The preferred ketal (Ab) is the ethylene ketal. The preferred enamines are selected from the group consisting of pyrrolidine, morpholine and diethylamino amines. The enol ethers (a) are prepared by methods well known in the art, see J. Org. Chem. 26, 3925 (1961), Steroid Reactions, Edited by Carl Djerassi, Holden-Day, San Francisco 1963, page 42-45, and U.S. Pat. No. 3,516,991 (Preparation 1). The ketals (b) are also prepared by well known methods, see Steroid Reactions, supra, page 11-14. The 3-enamines (c) are also prepared by methods well known in the art, see U.S. Pat. Nos. 3,629,298 and 4,216,159 and Steroid Reactions, supra, page 49-53.

The $\Delta^{1,4}$-3-keto steroids (B) do not have to have the $C_3$ ketone protected.

The 3-hydroxy steroid (C) should have the 3β-hydroxyl group protected as the ether (Ca), see Chart C. The preferred blocking groups are methyl, ethyl, ethoxy ethyl (EEE), tetrahydropyranyl (THP) and trimethylsilyl (TMS).

Monolithium acetylide is known, see M. M. Midland, J. Org. Chem. 40, 2250 (1975).

The monolithium acetylide can be prepared in different ways which is of importance because the reaction temperature is dependent on the method of preparation.

The monolithium acetylide can be prepared by bubbling acetylene through an etheral solvent such as THF at about 20°-25° until no further weight gain occurs (about 0.6M in acetylene). An aliquot of this solution is cooled to about −60° and 4 equivalents (per equivalent of steroid) of an organo-lithium reagent such as n-butyllithium or phenyllithium are added with vigorous stirring to give a mixture which is about 0.57M in monolithium acetylide. Temperatures above about −30° and concentrations above about 0.8M in monolithium acetylide cause disproportionation to the insoluble dilithium acetylide. Therefore, slow addition of pre-cooled (−20° or less) organo-lithium reagent to very cold solution of acetylene in a dry solvent such as THF, diethyl ether, or dioxane is preferred. It is preferred the temperature be kept at −80° to −25°, more preferably at −80° to −40°. If the organic solvent is at a temperature of −40° or warmer, the organo-lithium solution should be added slower using a higher stirring rate to facilitate heat transfer. The monolithium acetylide solution should be used immediately after preparing as letting it stand even at −78° for 6 hours may lower the yield 10%.

A stabilized monolithium acetylide is preferably used. It permits preparation and reaction with 16-methylene-17-keto steroids at higher temperatures which is commercially advantageous. The stabilized monolithium acetylide is prepared in 3 alternative ways, two-pot (preferred), one-pot or in situ.

In the two pot process, a sufficient quantity of acetylene is first dissolved in a suitable dry organic solvent. The temperature at which the acetylene can be dissolved in the dry organic solvent is not critical. The temperature affects the solubility and therefore the concentration of the acetylene. However, before the acetylene solution is contacted with the lithium complex it must be cooled to 0° or less. The nature of the organic solvent is not critical so long as it does not react with acetylene, organolithium compounds or amines. Suitable dry organic solvents include THF, dioxane, diethyl ether, t-butyl methyl ether and dimethoxyethane. The preferred solvent is THF. It is convenient for the organic solvent to be saturated with acetylene. Second, an organo-lithium compound is contacted with a stabilizing amine at 0° or less in a suitable dry organic solvent. Organo-lithium compounds include n-butyllithium, phenyllithium, and methyllithium, preferred is n-butyllithium. A stabilizing amine is an amine (primary, secondary or tertiary) which when reacted with an organo-lithium compound to form a lithium complex and/or corresponding lithium amide subsequently reacted with acetylene forms a stabilized monolithium acetylide which will not significantly disproportionate at 0° and below which is reactive towards 17-keto steroids. Stabilizing amines include N,N-diisopropyl ethyl amine, triethylamine, diisopropyl amine, t-butyl amine, diethylamine, dicyclohexylamine, hexamethyl disilazane, and pyrrolidine. Some amines such as pyrrolidine are only useful with some steroids such as 16β-methylandrosta-1,4,9(11)-triene-3,17-dione. Amines which are not operable include ethylenediamine and pyridine. Preferred is diisopropylamine or triethylamine. The same dry organic solvents useful to dissolve the acetylene in are also useful here. It is preferred that the same solvent or mixture of solvents be used for dissolving the acetylene in as for the reaction of the organo-lithium compound with the stabilizing amine. The reaction of the organo-lithium compound with a primary or secondary amine produces a lithium amide. A tertiary amine cannot produce a lithium amide and forms a complex, the nature of which is not known. Therefore, the reaction of an organo-lithium compound and a stabilizing amine will be considered to have produced a lithium complex. When the organo-lithium compound is added to the stabilizing amine it must be added slowly maintaining the temperature at about 25° or less. The reaction is complete in less than 30 min.

The third step of the two-pot process is contacting the lithium complex of step 2 with the acetylene solution of step 1 at 0° or less. It is preferred that the method of contacting be a slow addition of the lithium complex to the acetylene solution keeping the temperature at 0° or less. The reaction forming monolithium acetylide is complete in less than 30 min.

In the two-pot process, the first two steps which are independent of each other can be performed in the reverse order. The organo-lithium compound can be reacted with the stabilizing amine prior to the dissolving of the acetylene in the dry organic solvent. All that is necessary is that both steps be independently performed and the temperature of both mixtures be 0° or less before they are combined in the third step.

The 16-methylene-17-keto steroid (I) to be ethynylated is added to the monolithium acetylide at 0° or less. The ethynylation reaction is complete in less than 30 minutes. The 16-methylene-17-keto steroid (I) can be added as a solid, a slurry or as a solution. For convenience it is preferred that it be added as a solution. It should be added slowly as is known to those skilled in the art. Again, the same organic solvents used for steps 1 and 2 are useful for adding the material to be ethynylated to the monolithium acetylide. Again, it is preferable to use the same organic solvent as was used in steps 1 and 2. The ethynylated product is recovered by means well known to those skilled in the art.

In the one-pot process, the first step of dissolving the acetylene in a suitable dry organic solvent is the same as for the two-pot process. Second, the stabilizing amine is added to the acetylene solution at 0° or less. Third, the organo-lithium compound is added slowly to the mixture of the acetylene solution and the stabilizing amine again at 0° or less.

With the in situ process, the first step again is the same. Second, the 16-methylene-17-keto steroid (I) to be ethynylated is added to the acetylene solution at 0° or less. Third, the organo-lithium compound and the stabilizing amine are reacted to form the lithium complex as in the second step of the two-pot process. Finally, the lithium complex is added slowly to the mixture of the acetylene solution containing the 16-methylene-17-keto steroid (I) to be ethynylated at 0° or less and the monolithium acetylide is generated in situ.

While the above steps to prepare monolithium acetylide can be performed at 0° it is preferable to perform them at less than $-20°$, more preferably in a temperature range of about $-20°$ to about $-40°$. Reducing the temperature reduces the amount of disproportionation, thereby increasing the amount of monolithium acetylide available for ethynylation.

The above discussion involves the temperatures at which the monolithium acetylide is prepared. The main advantage of using stabilized monolithium acetylide over non-stabilized monolithium acetylide is that it can be prepared and reacted at warmer temperatures. The reaction temperature of the monolithium acetylide with the 16-methylene-17-keto steroids (I) is usually about the same as the preparation temperature. If the reaction is performed above the decomposition temperature of the reagent, the yield will decrease. In the $\Delta^{1,4}$-3-keto series (B) the reaction temperature must be lower than in the protected $\Delta^4$-3-keto (A) or 3-hydroxy (C) series because one must have selectivity for the monolithium acetylide with the $C_{17}$-ketone over the unprotected $C_3$-ketone. For the $\Delta^4$-3-keto (A) and 3-hydroxy (C) steroids in their $C_3$-protected form the ethynylation reaction is performed at about 0° or less, preferably at about $-20°$ or less, more preferably at about $-40°$ or less. For the $\Delta^{1,4}$-3-keto steroids (B) the ethynylation reaction is performed at about $-20°$ or less, preferably at about $-40°$ or less, more preferably at about $-50°$ or less.

With the $\Delta^{1,4}$-3-keto-16-methylene-17-keto steroids (IB) no $C_3$ protecting group is necessary. However, it is preferable to add at least one equivalent of lithium ion prior to contacting the 17-keto steroid (I) with the monolithium acetylide. The lithium ion helps keep the selectivity for the 17-ketone over the 3-ketone. The lithium ion is added as a lithium salt, for example, lithium chloride, lithium sulfate, etc. Preferred is lithium bromide or lithium perchlorate. Using the lithium ion with $\Delta^{1,4}$-3-keto-16-methylene-17-keto steroids (IB) permits the same yield and selectivity at about $-40°$ as was obtained without the lithium ion at about $-78°$.

Generally, slightly more than one equivalent of monolithium acetylide per equivalent of 16-methylene-17-keto steroid (I) is used. The more monolithium acetylide used up to 4 equivalents the better. Two equivalents are preferred and about four equivalents are more preferred.

When the acetylene addition is complete the excess acetylide is quenched or destroyed by reaction with a quenching agent which is any aqueous system such as water, saline or aqueous buffers depending on what final pH is desired. The preferred quenching agent is a buffer. The 17α-ethynyl-17β-hydroxy-16-methylene steroids (II) are obtained or isolated from the reaction mixture by means well known to those skilled in the art. In the case of the $\Delta^4$-3-keto steroids (A) and 3-hydroxy steroid (C) the 17α-ethynyl-17β-hydroxy-16-methylene steroids (IIA and IIC) can be isolated as the $C_3$ protected form. The $C_3$ protecting group is removed by means well known to those skilled in the art or the $C_3$ protecting group may be left on for further chemical modification of the 17α-ethynyl-17β-hydroxy-16-methylene steroid (II). Before the 17α-ethynyl-17β-hydroxy-16-methylene-steroid (II) is isolated the $C_3$ protecting group can be hydrolyzed in situ so as to obtain the unprotected or free 17α-ethynyl-17β-hydroxy-16-methylene steroid (II) by reaction with water and a proton source such as sulfuric acid or hydrochloric acid at 20°-25° as is known in the art. For example, if the 17-keto-16-methylene steroid (IA) is protected as the enol ether (a) the protecting group can be removed by acid so that the 17α-ethynyl-17β-hydroxy-16-methylene steroid (II) will be isolated in the free $\Delta^4$-3-keto form (A). The $\Delta^{1,4}$-3-keto steroids (B) are not protected and therefore the 17α-ethynyl-17β-hydroxy-16-methylene product (II) will be in the free or unprotected form. The $C_3$ protecting group is removed from the 3-hydroxy steroids (C) by reaction with a means for hydrolyzing the $C_3$ protecting group which in the case of the ethers (Ca) includes acids with a pKa of less than 4.0.

The 17α-ethynyl-17β-hydroxy-16-methylene steroids (II) are useful intermediates in the preparation of 17α-hydroxy-16-methylene-progesterones, see Chart D. The 17α-ethynyl-17β-hydroxy-16-methylene steroid (II) is transformed to the corresponding 17β-hydroxy steroid (III) by reaction with a mercuric agent. Oxymercuration of ethisterone derivatives is old, see Helv. Chim. Acta. 26, 680 (1943). However, the present D ring is not a simple ethisterone derivative. Here the 17α-ethynyl-17β-hydroxy substituents are allylic to a 16-methylene group. Surprisingly and unexpectedly quantitative yields of the 17β-hydroxy steroids (III) are obtained indicating that its allylic alcohol system did not compete with the propargyl alcohol system in the oxymercuration.

The mercuric agent can be produced by reaction of mercuric oxide with a strong acid such as sulfuric, hydrochloric, or nitric acid. The mercuric salts, mercuric sulfate, mercuric chloride or mercuric nitrate can be used directly in acid medium. Mercuric sulfate or this salt made from mercuric oxide and sulfuric acid is preferred. A catalytic amount of a mercuric agent and the 17α-ethynyl-17β-hydroxy-16-methylene steroid (II) are contacted at 20°–65° for 2–24 hr in an aqueous polar solvent. When the oxymercuration reaction is complete, the reaction mixture is filtered (thru Celite) to remove insoluble mercuric salt solids and the 17β-hydroxy steroid (III) is recovered from the filtrate by means well known to those skilled in the art. Alternatively the oxymercuration reaction can be performed using the mercuric agent affixed to a resin. See M. S. Newman, J. Am. Chem. Soc., 75, 4740 (1953).

The 17β-hydroxy steroids (III) are next converted to the corresponding sulfoxides (IV) by reaction with a sulfenylating agent of the formula $R_{22}$-S-M (V). It is preferred that M is a chlorine or bromine atom, more preferred that M be a chlorine atom. It is preferred that $R_{22}$ be methyl, phenyl, p-chlorophenyl, p-methoxyphenyl or p-methylphenyl. It is more preferred that $R_{22}$ be phenyl.

The appropriately substituted sulfenylating agents (VIII) are prepared by methods known to those skilled in the art. For example, sulfuryl chloride is added to a thiol previously dissolved in an organic solvent such as methylene chloride. See Chem. Reviews, 39, 269 (1946) at page 279 and U.S. Pat. No. 2,929,820.

The sulfenylation reaction is carried out in a nonpolar aprotic solvents such as toluene, chloroform, diethyl ether, or methylene chloride, THF, and dioxane or mixtures thereof. It is preferred that the solvent be methylene chloride. The reaction is carried out in the presence of at least an equal molar amount of a tertiary amine base, such as triethylamine, trimethylamine or pyridine. Trimethylamine is preferred. Any excess base serves as additional solvent for the reaction. The reaction is preferably carried out under an inert dry gas such as nitrogen, argon, or carbon dioxide. The substituted sulfenyl halide (V) is added dropwise to the reaction mixture at a temperature of −20° to −40°. Following addition of the substituted sulfenylating agent (V) to the reaction mixture, the excess substituted sulfenylating agent is quenched with an appropriate quenching agent such as water, cyclohexene, various alcohols such as methanol and ethanol, or acetone. The sulfoxide (IV) may be obtained by standard work-up.

The sulfoxide (IV) exists as 2 double bond isomers; the compound of formula (IV) and where the unsaturation is between $C_{16}$ and the carbon atom attached to the sulfur atom. The endocyclic isomer (IV) usually predominates with only small amounts of the exocyclic isomer. However, the ratio of the isomeric sulfoxides is unimportant as both isomers are converted to the same product in the next step.

The sulfoxides (IV) are converted to the corresponding 16-methylene-17α-hydroprogesterones (VI) by reaction with a thiophile with heat. The sulfoxides (IV) are placed in an appropriate solvent or mixture of solvents such as toluene, methanol, ethylene dichloride or acetone. Some thiophiles such as hydroxide, alkoxide, etc. produce undesirable side reactions; others such as trimethylphosphite and diethylamine and mixtures thereof are more suitable. The preferred thiophile is trimethylphosphite. Trimethylphosphite is known as a thiophile, see D. A. Evans & G. C. Andrews, Acct. of Chem. Res. 7, 147 (1974) at p. 150. The sulfoxide (IV) and thiophile are contacted and heated from about 50°–100° depending on solvent(s), sulfoxide (IV), thiophile, and whether or not the reaction is conducted under pressure. It is preferred to heat the reaction mixture from 60°–90° in a sealed reacting container for 4–24 hr. When the reaction is complete the 16-methylene-17α-hydroxyprogesterone (VI) is isolated and purified by means well known to those skilled in the art.

The 16-methylene-17α-hydroxyprogesterones (VI) are useful as intermediates in the production of commercial pharmaceutical agents in two ways. First, 16-methylene steroids are intermediates in the manufacture of certain progestational agents such as melengestrol acetate, and second where the 16-methylene group is reduced to 16α-methyl or 16β-methyl to give intermediates useful in the production of antiinflammatory corticoids. For example, androstenedione can be converted to melengestrol acetate, a 16-methylene steroid in the following manner: (1) androstenedione is converted to 6-methyleneandrost-4-ene-3,17-dione by the process of U.S. Pat. No. 3,642,840, Example 18; (2) 6-methyleneandrost-4-ene-3,17-dione is converted to 6-methylandrosta-4,6-diene-3,17-dione by the process of U.S. Pat. No. 3,117,966, Example 16; (3) 6-methylandrosta-4,6-diene-3,17-dione is converted to 6-methyl-16-methyleneandrosta-4,6-diene-3,17-dione (I) by the process of Hungarian Pat. No. 019,495, Gazz. Chim. Ital. 91, 672 (1961) or the above described process for transformation of a 17-keto steroid to the corresponding 16-methylene-17-keto steroid (U.S. Pat. No. 4,416,821; (4) 6-methyl-16-methyleneandrosta-4,6-diene-3,17-dione (IA) is converted to 17α-ethynyl-17β-hydroxy-6-methyl-16-methyleneandrosta-4,6-dien-3-one (IIA) by the process of the present invention, which is converted to 17α-hydroxy-6-methyl-16-methylenepregna-4,6-diene-3,20-dione (VI) as described above; and (5) acylation of the 17α-hydroxy-6-methyl-16-methylenepregna-4,6-diene-3,20-dione (VI) to 17-acetyloxy-6-methyl-16-methylenepregna-4,6-diene-3,20-dione (melengestrol acetate) by the process of U.S. Pat. No. 4,154,748, Example 12.

Alternatively, and preferably, the following sequence can be used: (1) 16-methyleneandrostenedione (IA, Hungarian Pat. No. 019,495, Example 3) is converted to 17α-ethynyl-3,17β-dihydroxy-16-methyleneandrosta-3,5-diene 3-methyl ether by the process of the present invention, then (2) the 17α-ethynyl-3,17β-dihydroxy-16-methyleneandrosta-3,5-diene 3-methyl ether is converted to 17α-ethynyl-17β-hydroxy-6,16-dimethyleneandrost-4-en-3-one by the process of U.S. Pat. No. 3,642,840, (3) the 17α-ethynyl-17β-hydroxy-6,16-dimethyleneandrost-4-en-3-one is then converted to the corresponding 17β-hydroxy steroid (III), sulfoxide (IV) and ultimately to 17α-hydroxy-6,16-dimethylenepregn-4-ene-3,20-dione (VI), which upon reaction with acetic anhydride and p-TSA forms 17α-acetyloxy-6-methyl-16-methylenepregna-4,6-diene-3,20-dione, melengestrol acetate.

The 16-methylene-17α-hydroxyprogesterones (VI) can readily be transformed into a 16-methylene corticoid by reaction with iodine, an excess of calcium oxide, an aqueous sodium hydroxide and potassium acetate in acetone as is well known, see for example H. J. Ringold, et al., J. Am. Chem. Soc. 80, 250 (1958), O. Halpern, et al., J. Am. Chem. Soc. 81, 439 (1959) and J. Org. Chem. 25, 1060 (1966). The 16-methylene corticoid can then be readily transformed to a 16β-methyl corticoid by the process of U.S. Pat. No. 3,115,508 or to a 16α-methyl corticoid by the process of U.S. Pat. No. 3,130,209.

For example, betamethasone (9α-fluoro-11β,17α,21-trihydroxy-16β-methylpregna-1,4-diene-3,20-dione) can be prepared from 17β-hydroxy-16-methylenepregna-1,4,9(11)-triene-3,20-dione (VI) by first transforming it to 17α,21-dihydroxy-16-methylenepregna-1,4,9(11)-triene-3,20-dione 21-acetate by the process of J. Am. Chem. Soc. 80, 250 (1958), J. Am. Chem. Soc. 81, 439 (1959) and J. Org. Chem. 25, 1966 (1960) and next transforming it to 17α,21-dihydroxy-16β-methylpregna-1,4,9(11)-triene-3,20-dione 21-acetate by the process of U.S. Pat. No. 3,115,508. The transformation of 17α,21-dihydroxy-16β-methylpregna-1,4,9(11)-triene-3,20-dione 21-acetate to betamethasone is described in U.S. Pat. No. 3,104,246, Examples I and II.

Dexamethasone (9α-fluoro-11β,17α,21-trihydroxy-16α-methylpregna-1,4-diene-3,20-dione) can also be prepared from 17β-hydroxy-16-methylenepregna-1,4,9(11)-triene-3,20-dione (VI) by first transforming it to 17α,21-dihydroxy-16-methylenepregna-1,4,9(11)-triene-3,20-dione 21-acetate as described above and next transforming it to 17α,21-dihydroxy-16α-methylpregna-1,4,9(11)-triene-3,20-dione 21-acetate by the process of U.S. Pat. No. 3,130,209. 17α,21-Dihydroxy-16α-methylpregna-1,4,9(11)-triene-3,20-dione 21-acetate is then epoxidized by means well known to those skilled in the art, see for example U.S. Pat. No. 3,980,778, Examples 2 and 7 to produce 9β,11β-epoxy-17α,21-dihydroxy-16α-methylpregna-1,4-diene-3,20-dione which is transformed to dexamethasone 21-acetate by the process of U.S. Pat. No. 3,007,932, Example 2.

Likewise diflorasone diacetate (6α,9α-difluoro-11β,17α,21-trihydroxy-16β-methylpregna-1,4-diene-3,20-dione 17,21-diacetate) can be produced using the process of the present invention. First, 6α-fluoro-11β-hydroxyandrosta-1,4-diene-3,17-dione (U.S. Pat. No. 2,867,630) is dehydrated to 6α-fluoroandrost-1,4,9(11)-triene-3,17-dione by means well known to those skilled in the art, see Steroid Reactions, C. Djerassi, Holden-Day, San Francisco, 1963 p. 238 & 239. The 16-methylene group is then added by the process of U.S. Pat. No. 4,416,821 to produce 6α-fluoro-16-methyleneandrosta-1,4,9(11)-triene-3,17-dione (IB) which is converted to 6α-fluoro-17α-hydroxy-16-methylenepregna-1,4,9(11)-triene-3,20-dione (VI). The 21-hydroxy function of the corticoids is next introduced as described above followed by transformation of the 16-methylene group to a 16β-methyl group also described above to give 6α-fluoro-17α,21-dihydroxy-16β-methylpregna-1,4,9(11)-triene-3,20-dione 21-acetate which is acylated according to the procedure described in U.S. Pat. No. 4,154,748 (Examples 6 and 7) to produce 6α-fluoro-17α,21-dihydroxy-16β-methylpregna-1,4,9(11)-triene-3,20-dione 17,21-diacetate (U.S. Pat. No. 3,980,778, Example 6). 6α-Fluoro-17α,21-dihydroxy-16β-methylpregna-1,4,9(11)-triene-3,20-dione-17,21-diacetate is then converted to diflorasone diacetate by the process of U.S. Pat. No. 3,980,778 (Examples 7 and 8).

DEFINITIONS

The definitions and explanations below are for the terms as used throughout the entire patent application including both the specification and claims.

All temperatures are in degrees Centigrade.

TLC refers to thin-layer chromatography.

THF refers to tetrahydrofuran.

THP refers to tetrahydropyranyl.

Saline refers to an aqueous saturated sodium chloride solution.

p-TSA refers to p-toluenesulfonic acid.

NMR refers to nuclear (proton) magnetic resonance spectroscopy, chemical shifts are reported in ppm (δ) downfield from tetramethylsilane.

TMS refers to trimethylsilyl.

EEE refers to ethoxy ethyl ether ($-O-CH_2CH_2OCHhd 2CH_3$).

TEA refers to triethylamine.

DME refers to dimethoxyethane.

When solvent pairs are used, the ratio of solvents used in volume/volume (v/v).

Androstenedione refers to androst-4-ene-3,17-dione.

Dexamethasone refers to 9α-fluoro-11β,17α,21-trihydroxy-16α-methylpregna-1,4-diene-3,20-dione.

Betamethasone refers to 9α-fluoro-11β,17α,21-trihydroxy-16β-methylpregna-1,4-diene-3,20-dione.

Melengestrol acetate refers to 17β-hydroxy-6-methyl-16-methylenepregna-4,6-diene-3,20-dione 17-acetate.

Monolithium acetylide refers to $LiC_2H$ and complexed forms thereof.

A stabilizing amine is an amine (primary, secondary or tertiary), which when reacted with an organo lithium compound to form a lithium complex and subsequently reacted with acetylene forms a stabilized monolithium acetylide which will not significantly disproportionate at 0° and below and which is reactive towards 17-keto steroids.

$R_3$ is alkyl of 1 thru 5 carbon atoms with the proviso that with the ketal (Ab) and enamine (Ac), the $R_3$ groups can be connected and when connected may be connected to an oxygen or nitrogen atom.

$R_3'$ is alkyl of 1 thru 3 carbon atoms, a TMS, THP or EEE group.

$R_6$ is a hydrogen or fluorine atom, methyl or methylene group. When $R_6$ is methylene, there is no 5-6 double bond in formula (A) or in formula (C).

$R_9$ is nothing, a hydrogen, fluorine or oxygen atom which makes the C-ring (a) $\Delta^{9(11)}$ when $R_9$ is nothing and (b) 9β,11β-epoxide when $R_9$ is an oxygen atom.

$R_{11}$ is a hydrogen or oxygen atom, two hydrogen atoms or α- or β-hydroxyl group which makes the C-ring (a) $\Delta^{9(11)}$ when $R_{11}$ is a hydrogen atom, (b) 9β,11β-epoxide when $R_{11}$ is an oxygen atom and ⋯⋯ between $C_{11}$ and $R_{11}$ is a single bond, and ⋯⋯

(c) a ketone when $R_{11}$ is an oxygen atom and between $C_{11}$ and $R_{11}$ is a double bond.

$R_{22}$ is alkyl of 1 thru 5 carbon atoms, trichloromethyl, phenyl, phenyl substituted with 1 thru 4 carbon atoms or substituted with 1 thru 3 nitro or trifluoromethyl groups, aralkyl of 7 thru 12 carbon atoms, or —N—$(R_{122})_2$.

$R_{122}$ is alkyl of 1 thru 4 carbon atoms, phenyl or phthalimide. ···· is a single or double bond.

~ indicates that the attached atom or group can be in either the α or β configuration.

Metal refers to lithium, sodium, potassium or magnesium.

When the term "alkyl of___ thru___ carbon atoms" is used, it means and includes isomers thereof where such exist and are operable.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

EXAMPLE 1

17α-Ethynyl-3,17β-dihydroxy-16-methyleneandrosta-3,5-diene 3-methyl ether (IIAa)

THF (400 ml) is cooled to −40°. Acetylene is sparged through the THF, with the temperature rising to −28° and then over 0.5 hour dropping to −36°. Acetylene bubbling is continued another 0.5 hour. The mixture is cooled to −43° and acetylene bubbled for an additional 0.5 hour. 3-Hydroxy-16-methyleneandrosta-3,5-dien-17-one 3-methyl ether (IAa, U.S. Pat. No. 4,416,821, Example 8, 40.0 g) is added with stirring maintaining the −50° cooling bath.

Diisopropylamine (44 ml) and THF (50 ml) are mixed and cooled to 8°. n-Butyl lithium (1.6M in hexane, 194 ml) is added at such a rate as to keep the exotherm below 25°. When the addition is complete, the lithium diisopropylamide mixture is transferred via a cannula to an addition funnel and then added dropwise to the steroid-acetylene mixture while maintaining the reaction temperature <−38° (bath temperature was −50°). When addition is complete (65 minutes) TLC indicates the reaction is approximately 98% complete. The reaction mixture is added slowly into saline/water (1 l, 1/1) and stirred. The layers are separated. The aqueous layer is extracted with ethyl acetate (200 ml). The organic phases are combined, washed with saline, dried over sodium sulfate after addition of triethylamine (1 ml) and concentrated under reduced pressure to a volume of about 80 ml. Methanol (200 ml) and triethylamine (1 ml) are added and the mixture concentrated under reduced pressure to about 100 ml. Methanol (200 ml) is added and the mixture again concentrated to about 100 ml. The mixture is filtered, the solids washed with cold methanol to give the title compound.

EXAMPLE 2

17α-Ethynyl-3,17β-dihydroxy-16-methyleneandrosta-3,5-diene 3-methyl ether (IIAa)

Dry THF (250 ml) previously cooled to −10° is sparged with acetylene until saturated.

Dry THF (50 ml) and diisopropylamine (44 ml) are cooled to −20°. n-Butyl lithium (1.6M, 194 ml) is added to the amine/THF mixture producing lithium diisopropyl amide. The lithium diisopropyl amide is slowly added to the acetylene maintaining the temperature at about −20° thereby producing monolithium acetylide.

3-Methoxy-16-methyleneandrosta-3,5-dien-17-one (IAa, U.S. Pat. No. 4,416,821, 50.0 g) in THF (250 ml) is added dropwise over a period of 30 min. to the monolithium acetylide maintaining the temperature at about −20°. TLC indicates the reaction is complete after about 15 minutes. The reaction mixture is then added to water (500 ml) containing sodium chloride (75 g) via a drop funnel and stirred 10 min. The two phases are separated and the aqueous phase back-extracted with ethyl acetate (200 ml). The ethyl acetate backwash is combined with the organic phase and the aqueous phase is discarded. The organic phase is washed with water (500 ml) containing sodium chloride (75 g), dried and concentrated under reduced pressure at less than 30° to a volume of about 175 ml. Methanol (200 ml), water (30 ml) and TEA (1 ml) are added. The mixture is concentrated to about 200 ml by distillation, cooled to 10°, stirred 10 min. and filtered. The solids are washed twice with methanol (2×50 ml) containing 15% water. The solids are dried overnight at 50° under reduced pressure to give the title compound (first crop). The mother liquor is concentrated under reduced pressure at less than 35° to one-half its volume, cooled to 10°, stirred 5 min. and filtered. The solids are washed twice with cold methanol (2×20 ml) containing 15% water, dried overnight at 50° under reduced pressure to give a second crop of the title compound.

EXAMPLE 3

17α-Ethynyl-17β-hydroxy-6β-(N-phenyl-N-ethylaminomethyl)-16-methyleneandrosta-4-en-3-one (IIA)

17α-Ethynyl-3,17β-dihydroxy-16-methyleneandrosta-3,5-diene 3-methyl ether (IIAa, Example 1, 5 g), ethyl aniline (2.05 ml), THF (37.5 ml), and formaldehyde (37%, 1.33 g) were mixed, p-TSA (140 mg) was added and the mixture stirred overnight at 20°–25°. TLC showed the reaction to be complete. Water (100 ml) was added, the mixture filtered, the solids washed twice with water/THF; 2/1, the solid material was dried under nitrogen for 5 hours to give the title compound. NMR (CDCl$_3$) 0.85, 1.31, 2.52, 5.23, 5.82, 6.7 and 7.2δ.

EXAMPLE 4

17α-Ethynyl-17β-hydroxy-6,16-dimethyleneandrosta-4-en-3-one (IIA)

17α-Ethynyl-17β-hydroxy-6-β-(N-phenyl-N-ethylaminomethyl)-16-methyleneandrosta-4-en-3-one (Example 3) in THF (20 ml) are mixed. Degassed hydrochloric acid (6N, 55 ml plus 20 ml THF) are added. The mixture is stirred overnight at 20°–25° under nitrogen, at which time TLC shows the reaction to be complete. Water (110 ml) is added, the mixture filtered, the solids washed with 10% hydrochloric acid, twice with water, once with 5% sodium bicarbonate, and three times with water to neutrality. Solids were then dried under nitrogen overnight to give the title compound.

EXAMPLE 5

17α-Acetyl-17β-hydroxy-6,16-dimethyleneandrosta-4-en-3-one (IIIA)

Mercuric oxide red (0.32 g) was mixed with sulfuric acid/water (sulfuric acid, 0.4 ml; water, 6.0 ml) and let stand overnight. 17α-Ethynyl-17β-hydroxy-6,16-dimethyleneandrosta-4-en-3-one (Example 4, 5.0 g) is mixed with THF (15 ml). The mercuric sulfate solution is added the reaction heated to 41°–49° over a period of 6 hrs at which time TLC indicates the reaction is completed. Sodium carbonate (0.79 g) in water (10 ml) is added and the mixture stirred for 5 min. Celite (5 g) is added and the mixture stirred ½ hr at 20°–25°. The mixture is filtered through Celite (5 g), the solids washed with methanol/THF; 1/1 (2×10 ml) and once with THF (10 ml), followed by methylene chloride (10 ml). The filtrate and washings are concentrated under reduced pressure to about 35 ml, at which point crystals begin forming. Methanol (50 ml) is added and the mixture again concentrated under reduced pressure and permitted to sit overnight at 20°–25° under nitrogen atmosphere. Water (500 ml) is added, slowly at first, with stirring over a period of 15 min. The mixture is filtered, the solids washed with water (3×20 ml), and hexane (2×10 ml). The solids were dried under nitrogen to give the title compound.

EXAMPLE 6

6-Methylene-16-(phenylsulfinylmethyl)pregna-4,16-diene-3,20-dione (IVA)

17α-Acetyl-17β-hydroxy-6,16-dimethyleneandrosta-4-en-3-one (Example 5, 8.0 g) is dissolved in methylene chloride (66 ml) and cooled to −20°. Trimethylamine (2.56 ml) at −20° and methylene chloride (5 ml) are mixed and the trimethylamine mixture transferred by syringe to the steroid solution. To the cold steroid solution was added phenylsulfonylchloride (1.0 equivalent) by a syringe pump over 1 hr. TLC shows the reaction approximately 80–85% complete. Phenylsulfonylchloride (0.25 equivalent) was added over approximately 10 min., TLC showing the reaction to be approximately 95% complete. Phenylsulfonylchloride (0.10 equivalent) was then added for a total of 1.35 equivalence, at which time TLC shows the reaction to be complete. Hydrochloric acid (10%, 40 ml) was added all at once, the temperature now being 7°, and the mixture stirred for about 10 min. The phases are separated. The aqueous portion is back-extracted with methylene chloride (10 ml). The organic extracts are washed with phosphate buffer (25 ml) and back-extracted with methylene chloride (10 ml). The organic extracts are combined, dired over sodium sulfate overnight at 20°–25°. This mixture is filtered and the filtrate concentrated under reduced pressure to an oil, which is the title compound.

EXAMPLE 7

17α-Hydroxy-6,16-dimethylenepregn-4-ene-3,20-dione (VIA)

6-Methylene-16-phenylsulfonylmethylpregna-4,16-diene-3,20-dione (Example 6, 2.0 g) is placed in a 30-ml vial under nitrogen. Toluene (20 ml), methanol (2.89 ml), TEA (0.181 ml) and trimethylphosphite 1.02 ml) are added. After 1 hr at 20°–25°, the sealed vial was plunged into a hot oil bath with a bath temperature of 90° which is stirred at 90° for 4 hrs, at which time TLC shows the reaction to be essentially complete. The reaction mixture is transferred to a separatory funnel and water (10 ml) is added. Ethyl acetate (10 ml) is added to the organic mixture, which is washed with water (2×10 ml). The aqueous portion is back-extracted with toluene/ethyl acetate: 1/1. After the phases are separated, the organic phase is filtered through sodium sulfate and the filtrate is concentrated under reduced pressure to a volume of about 8 ml. This concentrate is permitted to sit at 20°–25° for approximately ½ hr. The resulting crystals are washed down into a flask with toluene (2 ml) and cooled to 5° for 2 hrs, then to −20° for 48 hrs. The crystals were collected with toluene (−20°), then with hexane three times and dried under nitrogen to yield the title compound.

EXAMPLE 8

17α-Hydroxy-6-methyl-16-methylenepregna-4,6-diene-3,20-dione 17-acetate (Melengestrol acetate)

17α-Hydroxy-6,16-dimethylenepregna-4-ene-3,20-dione (Example 7, 50 mg) is slurried in toluene (1.5 ml). Acetic anhydride (95 μl, 7 equivalents) and p-TSA/water (8 mg, 0.3 equivalents) are added. The reaction vessel is capped and heated at 85° for 3 hrs 20 min., then pulled from the heat, cooled and TLC shows the reaction is approximately 70% complete. The reaction mixture is heated for an additional 3 hrs, permitted to stand at 20°–25° overnight, at which time TLC shows the reaction is complete. Hydrochloric acid (6N, 200 μl) is added and the mixture stirred 1 hr at 20°–25°. On work-up, the title compound is obtained.

EXAMPLE 9

17α-Hydroxy-16-methylenepregn-4-ene-3,20-dione (17α-hydroxy-16-methyleneprogesterone)

Following the general procedure of Examples 5–7 and making noncritical variations and starting with 17α-ethynyl-3,17β-dihydroxy-16-methyleneandrosta-3,5-diene 3-methyl ether (Example 1) the title compound is obtained.

EXAMPLE 10

17α-Ethynyl-3,17β-dihydroxy-16-methyleneandrost-3,5-dien 3-methyl ether (IIAa)

Dry THF (50 l) is cooled to −20° and acetylene (2.7 kg) is dissolved in the THF.

In a separate tank diisopropylamine (8.8 l) is dissolved in dry THF (10 l) and cooled to −20°. n-Butyllithium (1.6M in hexane, 38.8 l) is added slowly to the amine at −20±5°.

The lithium-amine mixture is added slowly to the acetylene solution at −20±5°.

3-Methoxy-16-methyleneandrost-3,5-dien-17-one (IAa, 10 kg) in THF (50 l) is added to the reaction mixture at or below −20° and stirred for 20 min to give the title compound.

EXAMPLE 11

17α-Ethynyl-3,17β-dihydroxy-16-methyleneandrosta-3,5-diene 3-methyl ether (IIAa)

Dry THF (250 ml) is cooled to −10° and sparged with acetylene until saturated. The acetylene addition was stopped and the solution cooled to −20° where diisopropylamine (44 ml) is added while maintaining −20°. n-Butyllithium (1.6M, 194 ml) is then added, also maintaining −20°, and the resulting mixture stirred at −20° for 30 minutes.

3-Methoxy-16-methyleneandrosta-3,5-diene-17-one (IAa, U.S. Pat. No. 4,416,821, 50.0 g) in dry THF (200 ml) is added dropwise over a period of 30 minutes as the temperature is kept at about −20°. Fifteen minutes after addition, saline (500 ml) is added to quench the reaction which was worked up in the same manner as Example 2 to give the title compound.

EXAMPLE 12

17α-Ethynyl-3,17β-dihydroxy-16-methyleneandrosta-3,5-diene 3-methyl ether (IIAa)

A cold (−10°) solution of dry THF (250 ml) is saturated with acetylene over 1½ hours. The acetylene addition is stopped and the solution cooled further to −20°. Triethylamine (44 ml) is added, followed by n-butyllithium (1.6M, 194 ml) while maintaining −20°, and the resulting mixture stirred at −20° for 30 minutes.

3-Methoxy-16-methyleneandrosta-3,5-diene-17-one is added over 30 minutes, maintaining about −20°. Fifteen minutes after addition, TLC shows the reaction to be complete, so the reaction mixture is dumped into saline (500 ml) and worked up in the same manner as Example 2 to give the title compound.

EXAMPLE 13

17α-Ethynyl-3,17β-dihydroxy-16-methyleneandrosta-3,5-diene 3-methyl ether (IIAa)

Dry THF (250 ml) is cooled to −10° and saturated with acetylene. The acetylene addition is stopped and the solution cooled to −20°.

In another flask, triethylamine (43.8 ml) and THF (50 ml) are mixed and cooled to −20°. n-Butyllithium (1.6M, 194 ml) is added, maintaining about −20°, and the resulting mixture added over 25 minutes at −20° to the acetylene-THF solution. The cloudy solution was stirred 30 minutes at −20°.

3-Methoxy-16-methyleneandrosta-3,5-diene-17-one (IAa, U.S. Pat. No. 4,416,821, 50.0 g) in dry THF (250 ml) is added over 30 minutes maintaining −20°, then stirred 15 minutes at −20°. TLC shows the reaction to be complete, so the mixture is dumped into saline (500 ml) and worked up in the same manner as Example 2 to give the title compound.

EXAMPLE 14

17α-Ethynyl-3,17β-dihydroxy-16-methyleneandrosta-3,5-diene 3-methyl ether (IIAa)

Dry THF (450 ml) is saturated at 20°–25° with acetylene, then cooled quickly to −70°. Acetylene addition is stopped and n-butyllithium (1.6M, 150 ml) is added over about 45 minutes, while maintaining −68°. The mixture is then warmed to −35° over about 30 minutes where 3-methoxy-16-methyleneandrosta-3,5-diene-17-one (IAa, U.S. Pat. No. 4,416,821, 30.0 g) in dry THF (150 ml) is added over about 15 minutes. The addition increased the temperature of the reaction mixture to −25°. After an additional 10 minutes, the reaction mixture is slowly added to cold pH 7 phosphate buffer (0.8N, 1000 ml). Ethyl acetate (500 ml) is added and the layers are separated. The organic layer is washed with saline (2×300 ml) and the aqueous layers are back-extracted with ethyl acetate (2×300 ml). The combined organic layers are dried and concentrated under reduced pressure to a solid which is triturated from boiling methanol (100 ml), cooled, filtered, and washed with cold methanol to give, after drying under reduced pressure at 42°, the title compound. A second crop is obtained in a similar manner by concentration of the mother liquors to a thick slurry, filtration, and washing with cold methanol, followed by drying under reduced pressure at 42°.

CHART A

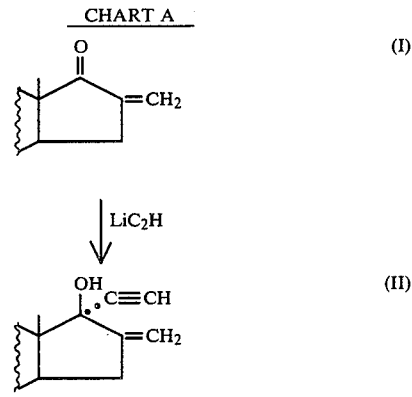

CHART B

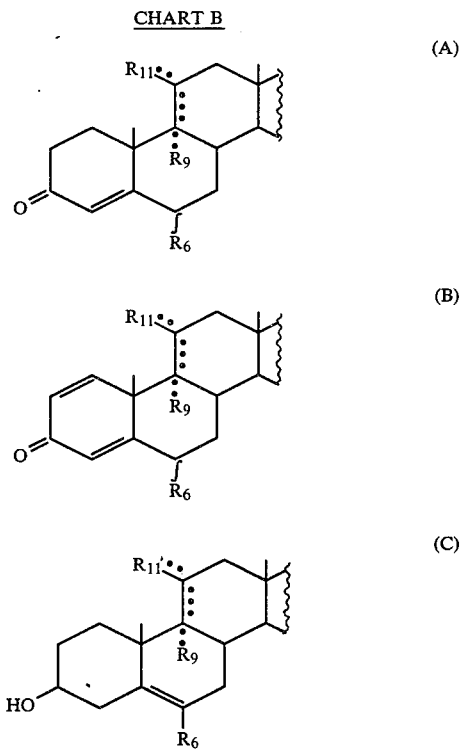

CHART C

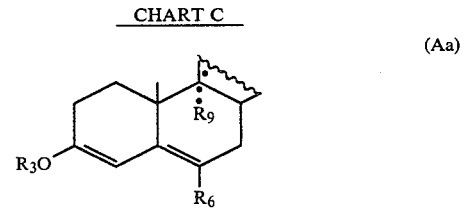

-continued
CHART C

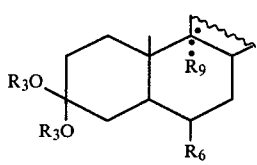
(Ab)

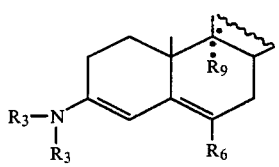
(Ac)

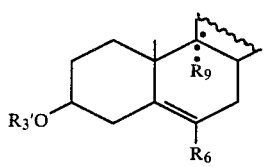
(Ca)

CHART D

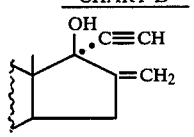
(II)

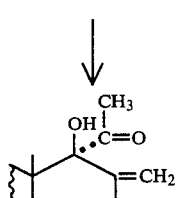
(III)

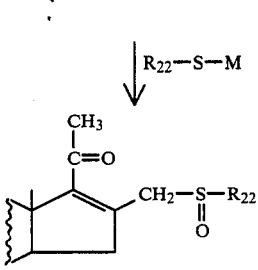
(V)
(IV)

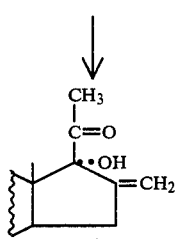
(VI)

I claim:
1. A process for the preparation of a $C_3$ protected 17α-ethynyl-17β-hydroxy-16-methylene steroid of the formula

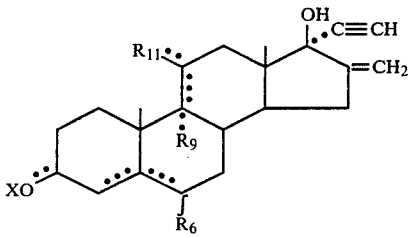
(II A,C)

which comprises
(1) contacting a $C_3$ protected 17-keto-16-methylene steroid of the formula

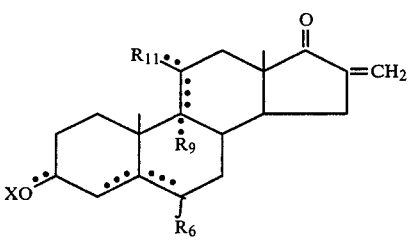
(I A,C)

with stabilized monolithium acetylide in a dry solvent at a temperature of about 0° or less;
(2) maintaining the reaction temperature at about 0° or less; and
(3) quenching with a quenching agent where
$R_6$ is a hydrogen or fluorine atom, methyl or methylene group; when $R_6$ is methylene, there is no 5–6 double bond in formula (A) or in formula (C);
$R_9$ is nothing, a hydrogen, fluorine or oxygen atom which makes the C-ring
  (a) $\Delta^{9(11)}$ when $R_9$ is nothing and
  (b) 9β,11β-epoxide when $R_9$ is an oxygen atom;
$R_{11}$ is a hydrogen or oxygen atom, two hydrogen atoms or α- or β-hydroxyl group which makes the C-ring
  (a) $\Delta^{9(11)}$ when $R_{11}$ is a hydrogen atom,
  (b) 9β,11β-epoxide when $R_{11}$ is an oxygen atom and between $C_{11}$ and $R_{11}$ is a single bond, and
  (c) a ketone when $R_{11}$ is an oxygen atom and between $C_{11}$ and $R_{11}$ is a double bond;
X is a hydrogen atom or nothing, when X is nothing, the at $C_3$ is a double bond, when X is a hydrogen atom, the at $C_3$ is a single bond; is a single or double bond; and
~ indicates that the attached atom or group can be in either the α or β configuration.

2. A process according to claim 1 where the $\Delta^4$-3-keto steroid (A)

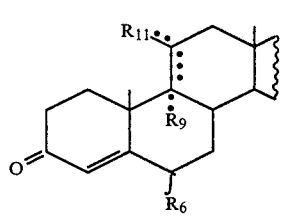
(A)

is in the $C^3$ protected form selected from the group consisting of compounds of the formula
enol ether

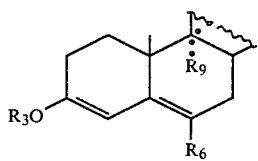
(Aa)

ketal

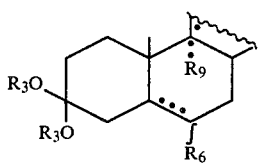
(Ab)

or enamine

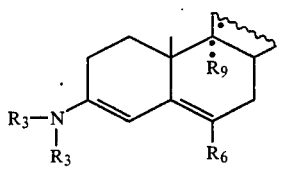
(Ac)

the $3\beta$-hydroxy-$\Delta^5$ steroid of the formula

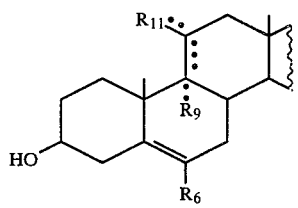
(C)

is in its $C_3$ protected form
ether

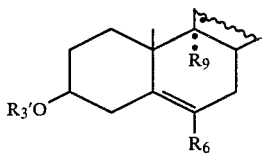
(Ca)

where
$R_3$ is alkyl of 1 thru 5 carbon atoms with the proviso that with the ketal (Ab), and the enamine (Ac), the $R_3$ groups can be the same or different and can be connected;
$R_3'$ is alkyl of 1 thru 3 carbon atoms, a TMS, THP or EEE group;
$R_6$ is a hydrogen or fluorine atom, methyl or methylene group; when $R_6$ is methylene, there is no 5-6 double bond in formula (A) or in formula (C);
$R_9$ is nothing, a hydrogen, fluorine or oxygen atom which makes the C-ring
 (a) $\Delta^{9(11)}$ when $R_9$ is nothing and
 (b) $9\beta,11\beta$-epoxide when $R_9$ is an oxygen atom;
$R_{11}$ is a hydrogen or oxygen atom, two hydrogen atoms or $\alpha$- or $\beta$-hydroxyl group which makes the C-ring
 (a) $\Delta^{9(11)}$ when $R_{11}$ is a hydrogen atom,
 (b) $9\beta,11\beta$-epoxide when $R_{11}$ is an oxygen atom and ⋯ between $C_{11}$ and $R_{11}$ is a single bond, and
 (c) a ketone when $R_{11}$ is an oxygen atom and ⋯ between $C_{11}$ and $R_{11}$ is a double bond; ⋯ is a single or double bond; and
~ indicates that the attached atom or group can be in either the $\alpha$ or $\beta$ configuration.

3. A process according to claim 1 where the dry solvent is selected from the group consisting of THF, dioxane, diethyl ether, t-butyl methyl ether, DME, and mixtures thereof.

4. A process according to claim 1 where the temperature is about $-20°$ or less.

5. A process according to claim 1 where the temperature is about $-40°$ or less.

6. A process according to claim 1 where the quenching agent is an aqueous medium selected from the group consisting of water, saline, aqueous buffers and mixtures thereof.

7. A process according to claim 1 where greater than 1 equivalent of monolithium acetylide is used.

8. A process according to claim 1 where the $17\alpha$-ethynyl-$17\beta$-hydroxy-16-methylene steroid (II) is $17\alpha$-ethynyl-$3,17\beta$-dihydroxy-16-methyleneandrosta-3,5-diene 3-methyl enol ether.

9. A process according to claim 1 where the stabilized monolithium acetylide is stabilized by an amine selected from the group consisting of N,N-diisopropylethylamine, triethylamine, diisopropylamine, t-butylamine, diethylamine, dicyclohexylamine, and hexamethyl disilazane.

10. A process according to claim 1 where the amine is diisopropylamine or triethylamine.

11. A process for the preparation of a $17\alpha$-ethynyl-$17\beta$-hydroxy-16-methylene steroid of the formula

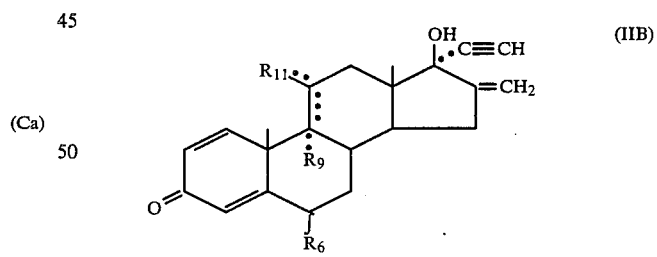
(IIB)

which comprises
(1) contacting a 17-keto steroid of the formula

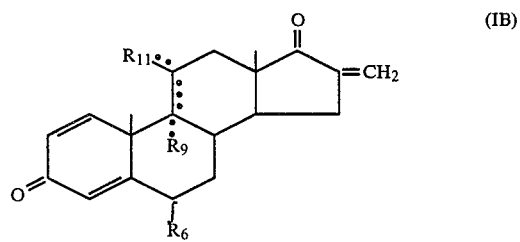
(IB)

with stabilized monolithium acetylide in a dry solvent at a temperature of about $-20°$ or less;

(2) maintaining the reaction temperature at about $-20°$ or less; and (3) quenching with a quenching agent where $R_6$ is a hydrogen or fluorine atom, methyl or methylene group; when $R_6$ is methylene, there is no 5-6 double bond in formula (A) or in formula (C);

$R_9$ is nothing, a hydrogen, fluorine or oxygen atom which makes the C-ring
  (a) $\Delta^{9(11)}$ when $R_9$ is nothing and
  (b) $9\beta,11\beta$-epoxide when $R_9$ is an oxygen atom;

$R_{11}$ is a hydrogen or oxygen atom, two hydrogen atoms or $\alpha$- or $\beta$-hydroxyl group which makes the C-ring
  (a) $\Delta^{9(11)}$ when $R_{11}$ is a hydrogen atom,
  (b) $9\beta,11\beta$-epoxide when $R_{11}$ is an oxygen atom and ･･･ between $C_{11}$ and $R_{11}$ is a single bond, and
  (c) a ketone when $R_{11}$ is an oxygen atom and ･･･ between $C_{11}$ and $R_{11}$ is a double bond;

X is a hydrogen atom or nothing, when X is nothing, the ･･･ at $C_3$ is a double bond, when X is a hydrogen atom, the ･･･ at $C_3$ is a single bond;

･･･ is a single or double bond; and

~ indicates that the attached atom or group can be in either the $\alpha$ or $\beta$ configuration.

12. A process according to claim 11 where the dry solvent is selected from the group consisting of THF, dioxane, diethyl ether, t-butyl methyl ether, DME, and mixtures thereof.

13. A process according to claim 11 where the temperature is about $-40°$ or less.

14. A process according to claim 11 where the temperature is about $-50°$ or less.

15. A process according to claim 11 where the quenching agent is an aqueous medium selected from the group consisting of water, saline, aqueous buffers and mixtures thereof.

16. A process according to claim 11 where greater than 1 equivalent of monolithium acetylide is used.

17. A process according to claim 11 where the stabilized monolithium acetylide is stabilized by an amine selected from the group consisting of N,N-diisopropylethylamine, triethylamine, diisopropylamine, t-butylamine, diethylamine, dicyclohexylamine, and hexamethyl disilazane.

18. A process according to claim 11 where the amine is diisopropylamine or triethylamine.

19. A process according to claim 11 where at least one equivalent of lithium ion is added prior to contacting the 17-keto steroid (IB) with the monolithium acetylide.

20. A process according to claim 19 where the lithium ion is added as lithium bromide, lithium perchlorate, lithium chloride or lithium sulfate.

* * * * *

UNITED STATES PATENT OFFICE
CERTIFICATE OF CORRECTION

Patent No. 4,614,621                              Dated   September 30, 1986

Inventor(s)   Verlan H. VanRheenen

It is certified that error appears in the above-identified patent and that said Letters Patent are hereby corrected as shown below:

Column 8, line 10, "hydroprogesterones" should read --hydroxyprogesterones--
Column 10, line 28, "H$_2$OCHhd 2CH$_3$" should read --H$_2$OCH$_2$CH$_3$--
Column 10, line 32, "in" should read --is--
Column 10, line 38, "17β-" should read --17α- --
Column 10, line 68, "bond, and ...." should read -- bond, and      --
Column 11, line 1, "and" should read --and ....--
Column 17, Chart C (Ab) " 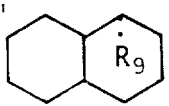 " should read -- 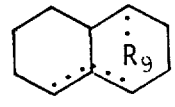 --

Column 17, line 67, "7α-" should read --17α- --
Column 17, line 68, "ormula" should read --formula--
Column 18, line 46, "and         between" should read --and .... between--
Column 18, line 49, "and         between" should read --and .... between--
Column 18, line 51, "the         at" should read --the .... at--
Column 18, line 52, "the         at" should read --the .... at--
Column 18, line 53, "     is a" should read --.... is a--
Column 19, (Ab) " 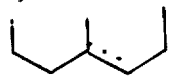 " should read -- 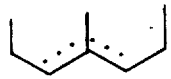 --

Column 21, line 26, "the .... at" should read --the .... at--

Signed and Sealed this

Seventeenth Day of February, 1987

Attest:

DONALD J. QUIGG

Attesting Officer            Commissioner of Patents and Trademarks